United States Patent
Andersen et al.

(10) Patent No.: US 11,761,873 B2
(45) Date of Patent: Sep. 19, 2023

(54) METHOD TO PREDICT DOWNHOLE RESERVOIR FLUIDS INTERFACIAL TENSION

(71) Applicant: SCHLUMBERGER TECHNOLOGY CORPORATOIN

(72) Inventors: Simon Ivar Andersen, Tikoeb (DK); Wael Abdallah, Al-Khobar (SA); Dominic Joseph Brady, Al-Khobar (SA); Mohammed Badri, Al-Khobar (SA); Sharath Chandra Mahavadi, Lexington, MA (US); Bastian Sauerer, Al-Khobar (SA); Mohamed Ahmed Abdel Reheem Hamdy, Dhahran (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 67 days.

(21) Appl. No.: 16/469,388

(22) PCT Filed: Dec. 14, 2017

(86) PCT No.: PCT/US2017/066241
§ 371 (c)(1),
(2) Date: Jun. 13, 2019

(87) PCT Pub. No.: WO2018/112116
PCT Pub. Date: Jun. 21, 2018

(65) Prior Publication Data
US 2020/0096429 A1    Mar. 26, 2020

Related U.S. Application Data

(60) Provisional application No. 62/434,286, filed on Dec. 14, 2016.

(51) Int. Cl.
*G01N 13/02* (2006.01)
*E21B 49/08* (2006.01)
(Continued)

(52) U.S. Cl.
CPC ............ *G01N 13/02* (2013.01); *E21B 47/114* (2020.05); *E21B 49/08* (2013.01); *E21B 49/081* (2013.01);
(Continued)

(58) Field of Classification Search
CPC .... G01N 13/02; G01N 21/33; G01N 21/3577; G01N 21/552; G01N 21/59; G01N 21/64;
(Continued)

(56) References Cited

U.S. PATENT DOCUMENTS

| | | | |
|---|---|---|---|
| 3,796,266 A | 3/1974 | Carlin et al. | |
| 5,859,430 A * | 1/1999 | Mullins | E21B 49/10 250/343 |

(Continued)

FOREIGN PATENT DOCUMENTS

| | | |
|---|---|---|
| EP | 1656549 A1 | 5/2006 |
| GB | 2513310 B | 10/2014 |

(Continued)

OTHER PUBLICATIONS

Yarranton et al., "Gibbs-Langmuir Model for Interfacial Tension of Nonideal Organic Mixtures over Water", 1996, J. Phys. Chem, 100,5,1786-1792. (Year: 1996).*

(Continued)

*Primary Examiner* — Samuel P Siefke
*Assistant Examiner* — Henry H Nguyen
(74) *Attorney, Agent, or Firm* — Jeffrey D. Frantz

(57) ABSTRACT

Methods may include emplacing a downhole tool within a wellbore, sampling a fluid downhole with the downhole tool; analyzing the fluid, and calculating an interfacial (Continued)

tension (IFT), wherein calculating the acid-base IFT contribution comprises measuring a concentration of a surface-active species directly. Apparatuses for measuring an interfacial tension (IFT) in a fluid downhole may be part of a downhole tool and may include a sampling head to sample the fluid; and a downhole fluid analysis module that includes a spectrometer capable of measuring a concentration of a surface-active species in the fluid, and a processor configured to determine the IFT of the fluid downhole based on the measured concentration of the surface-active species.

18 Claims, 14 Drawing Sheets

(51) Int. Cl.
　　　G01N 21/33　　　(2006.01)
　　　G01N 21/3577　　(2014.01)
　　　G01N 21/552　　 (2014.01)
　　　G01N 21/59　　　(2006.01)
　　　G01N 21/64　　　(2006.01)
　　　G01N 21/77　　　(2006.01)
　　　G01N 33/28　　　(2006.01)
　　　E21B 47/113　　 (2012.01)

(52) U.S. Cl.
　　　CPC ......... *G01N 21/33* (2013.01); *G01N 21/3577* (2013.01); *G01N 21/552* (2013.01); *G01N 21/59* (2013.01); *G01N 21/64* (2013.01); *G01N 21/77* (2013.01); *G01N 33/2823* (2013.01); *E21B 49/0875* (2020.05); *G01N 2013/0283* (2013.01); *G01N 2021/6417* (2013.01)

(58) Field of Classification Search
　　　CPC ............... G01N 21/77; G01N 33/2823; G01N 2013/0283; G01N 2021/6417; E21B 49/08; E21B 47/00; E21B 49/081; E21B 49/0875; E21B 47/113
　　　See application file for complete search history.

(56) References Cited

U.S. PATENT DOCUMENTS

| | | | |
|---|---|---|---|
| 6,118,520 A | 9/2000 | Harner | |
| 7,526,953 B2 * | 5/2009 | Goodwin | E21B 47/10 250/255 |
| 7,750,302 B2 * | 7/2010 | Jamaluddin | E21B 49/08 250/339.12 |
| 2001/0055115 A1 * | 12/2001 | Garver | G01J 3/20 356/328 |
| 2008/0037006 A1 | 2/2008 | Canas Triana et al. | |
| 2010/0269579 A1 * | 10/2010 | Lawrence | G01N 33/2823 73/152.23 |
| 2013/0337568 A1 * | 12/2013 | Pacheco E Silva | G01N 21/3151 436/72 |
| 2015/0047979 A1 | 2/2015 | Mahavadi et al. | |
| 2015/0114837 A1 | 4/2015 | Mahavadi et al. | |
| 2017/0067810 A1 | 3/2017 | Stukan et al. | |

FOREIGN PATENT DOCUMENTS

| | | | |
|---|---|---|---|
| WO | WO-0057158 A1 * | 9/2000 | ........... G01N 21/534 |
| WO | 2016018229 A1 | 2/2016 | |

OTHER PUBLICATIONS

Sahoo et al., "Surface Tension of Binary Metal Surface Active Solute Systems under Conditions Relevant to Welding Metallurgy", 1988, Metallurgical Transactions B, 19B (Year: 1988).*

Liu, et al., "Effect of active species in crude oil on the interfacial tension behavior of alkali/synthetic surfactants/ crude oil systems", 2008, Pet. Sci. 353-358 (Year: 2008).*

Andersson et al., "First-Principles Prediction of Liquid/Liquid Interfacial Tension", 2014, J. Chem. Theory Comput., 10, 8, 3401-3408 (Year: 2014).*

Abdallah, W. et al., "Sensitivity Analysis of Interfacial Tension on Saturation and Relative Permeability Model Predictions," SPE 149038, 2011, presented at the SPE/DGS Saudi Arabia Section Technical Symposium and Exhbition, Al-Khobar, Saudi Arabia, pp. 1-12.

Andersen, S. I. et al,"Detection and Impact of Carboxylic Acids at the Crude Oil-Water Interface", Energy Fuels, 2016, 30, pp. 4475-4485.

Andreas, J. M., "Boundary Tension by Pendant Drops", Journal of Physical Chemistry, 1938, 42, pp. 1001-1019.

Asar, H. et al., "Influence of Interfacial Tension on Gas/Oil Relative Permeability in a Gas-Condensate System," SPE 11740, SPE Reservoir Engineering, 1998, pp. 257-264.

"Standard Test Method for Acid Number of Petroleum Products by Potentiometric Titration", ASTM D664, Last updated Jan. 2019, 11 pages.

Axetris AG, [https://www.axetris.com/en-cn/irs/products/emirs200/to39-with-reflector4/#ScrollTo=0C215E67A328E737C2AF97D3D9290BDB] downloaded Apr. 1, 2020, 3 pages.

Bourdet, J. et al., "Fluorescence and Infrared Spectroscopy of Inclusion Oil", 2012, CSIRO, 60 pages.

Coats, K. H., "An Equation of State Compostional Model", SPE 8284-PA, Society of Petroleum Engineers Journal, 1980, pp. 363-376.

"35.6 x 10 x 2mm 45° ATR Prism" from Crystran ltd, [http://www.crystran.co.uk/prisms-and-atr/krs5-atr-prisms/356-x-10-x-2mm-45-atr-prism] downloaded Apr. 8, 2020, 2 pages.

Du Nouy, P. L., "A New Apparatus for Measuring Surface Tension," Journal of Genetic Physiology, 1919, 4 pages.

Haniff, M. S. et al., "Measuring Interfacial Tensions in a Gas-Condensate System with Laser-Light-Scattering Technique," SPE 19025-PA, SPE Reservoir Engineering, 1990, pp. 589-594.

Huh, C. et al.,"A rigorous theory of ring tensiometry", Colloid and Polymer Science, 1975, 253, pp. 566-580.

Kamel, M. Y. et al. "A Colorimetric Method for the Determination of Carboxylic Acids" Microchemical Journal, 1978, 23, pp. 445-452.

Ling, K. et al., "A New Correlation to Calculate Oil-Water Interfacial Tension", SPE 163328, presented at the SPE Kuwait International Petroleum Conference and Exhibition held in Kuwait City, Kuwait, 2012, 9 pages.

Liu N. et al., "A Method for the Determination of Weak Acid Concentration Based on Electrochemical Reduction of Benzoquinone", Journal of The Electrochemical Society, 2016, 163(5), pp. H373-H376.

MacLeod, D. B., 1923, "On a Relation Between Surface Tension and Density," Transactions of the Faraday Society, 1923, 19, pp. 38-41.

Stauffer, C. E., 1965, "The Measurement of Surface Tension by the Pendant Drop Technique", The Journal of Physical Chemistry, 1965, 69(6), pp. 1933-1938.

Sutton, R. P., 2006, "Petroleum Engineering Handbook, General Engineering," Richardson, TX, Society of Petroleum Engineering, pp. 257-331.

Sutton, R. P., "An Improved Model for Water-Hydrocarbon Surface Tension at Reservoir Conditions", SPE 124968, presented at the 2009 Annual Technical Conference and Exhibition, New Orleans, Louisiana, USA, pp. 1-18.

Varadaraj, R. et al., "Molecular Origins of Heavy Crude Oil Interfacial Activity Part 2: Fundamental Interfacial Properties of Model Naphthenic Acids and Naphthenic Acids Separated from Heavy Crude Oils", Energy & Fuels, 2007, 21(1), pp. 199-204.

(56) References Cited

OTHER PUBLICATIONS

Weinaug, C. F., Katz, D. L., "Surface Tensions of Methane-Propane Mixtures", Industrial and Engineering Chemistry, 1943, 35, pp. 239-246.

Zuidema, H. H. et al., 1941, "Ring Method for the Determination of Interfacial Tension," Industrial and Engineering Chemistry, 13, pp. 312-313.

Zuo, Y.-X. et al., "Prediction of Interfacial Tension of Reservoir Crude Oil and Gas Condensate Systems," SPE 38434, SPE Journal, 1998, pp. 134-145.

Notification of Transmittal of the international search report and the written opinion of the international searching Authority, or the Declaration, dated Mar. 14, 2018 (filed on Dec. 14, 2017, No. PCT/US2017/066241).

Notification concerning transmittal of international Preliminary Report on Patentability (Chapter I of the Patent Cooperation Treaty), dated Jun. 27, 2019 (filed on Dec. 14, 2017, No. PCT/US2017/066241).

Seifert et al, 1969, "Preparative thin-layer chromatography and high-resolution mass spectrometry of crude oil carboxylic acids," Anal. Chem. 1969, 41, 6, 786-795.

Examination Report issued in GB1910053.6, dated Mar. 19, 2021 (3 pages).

\* cited by examiner

FIG. 2.1
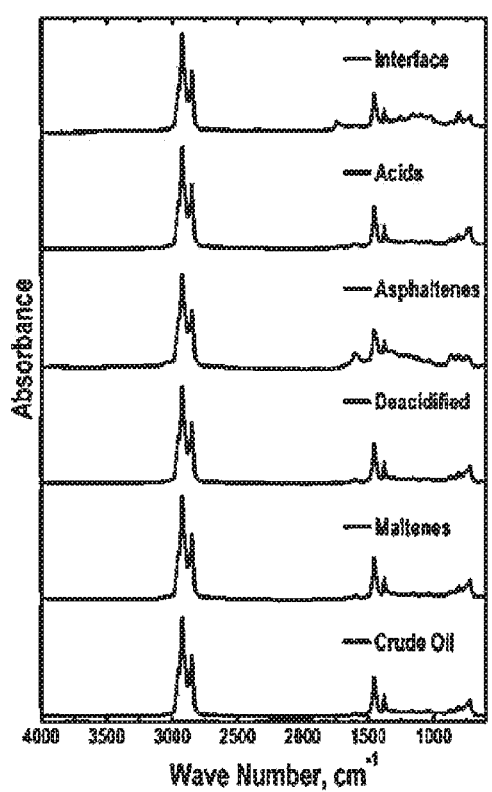
FIG. 2.2
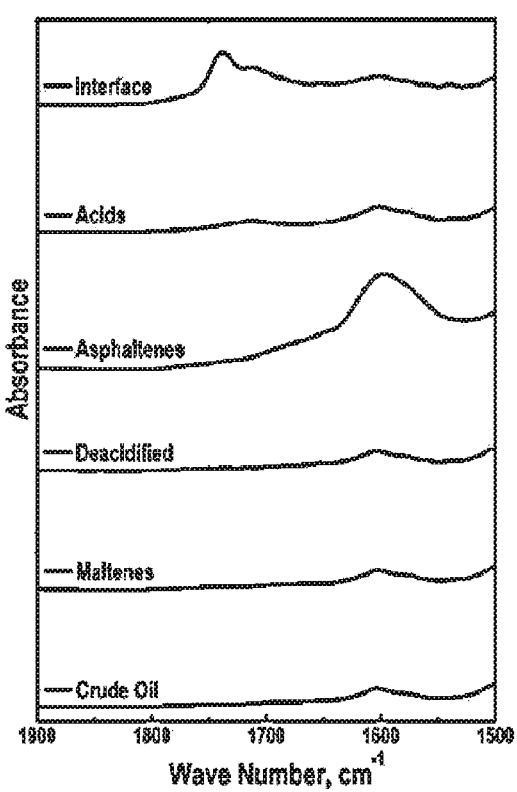

FIG. 11.1
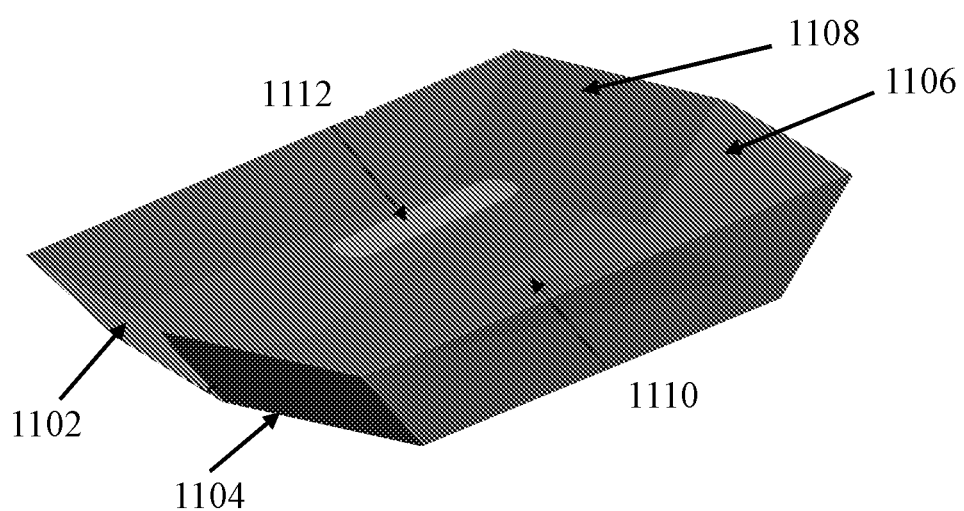
FIG. 11.2
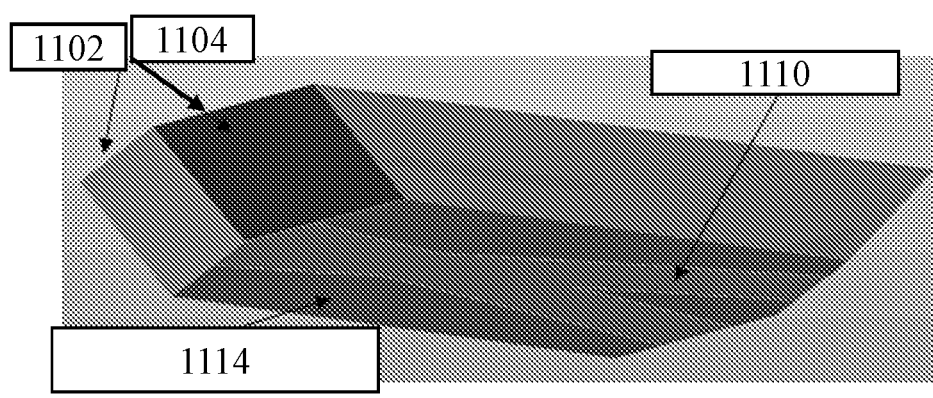

FIG. 13.1
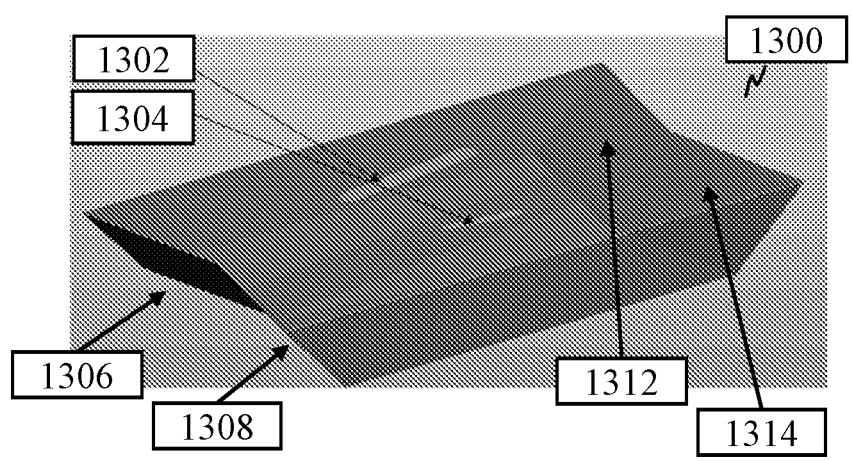
FIG. 13.2
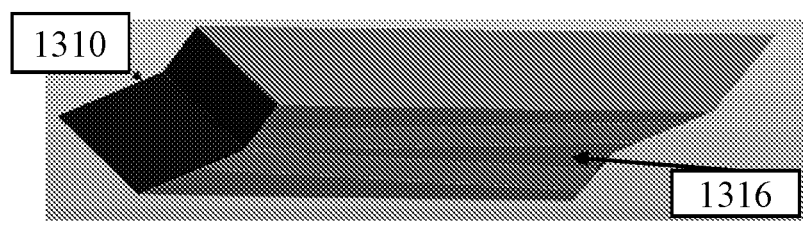

US 11,761,873 B2

METHOD TO PREDICT DOWNHOLE RESERVOIR FLUIDS INTERFACIAL TENSION

CROSS-REFERENCE TO RELATED APPLICATIONS

This application claims priority under 35 U.S.C. § 119(e) to U.S. Provisional Application No. 62/434,286 filed Dec. 14, 2016, which is incorporated herein by reference in its entirety.

BACKGROUND

The rate of oil recovery from hydrocarbon reservoirs is governed by the interplay of viscous and capillary forces that determine the fluid transport in porous media. Surface active constituents of the reservoir fluids may also accumulate at oil-brine and oil-rock interfaces and thus change the properties of the interfacial boundaries and the flow characteristics. Changes at the interphase boundaries affect the interfacial tension (IFT) and surface wettability. In order to get an accurate estimation of residual oil saturation and recoverable oil, a good knowledge of reservoir fluids IFT and reservoir rock wettability is an important factor. IFT depends on temperature, pressure, and fluid composition of a potential hydrocarbon source under reservoir conditions.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to methods that include emplacing a downhole tool within a wellbore; sampling a fluid downhole with the downhole tool; analyzing the fluid; and calculating an interfacial tension (IFT) for the fluid according to the formula: $\gamma = \gamma_{HC} + \gamma_{AB}$, wherein $\gamma_{AB}$ is the acid-base IFT contribution and $\gamma_{HC}$ is the hydrocarbon fluid IFT contribution, and wherein calculating the acid-base IFT contribution comprises measuring a concentration of a surface active species directly.

In another aspect, embodiments disclosed herein relate to apparatuses for measuring an interfacial tension (IFT) in a fluid downhole, the apparatus including a downhole tool, wherein the downhole tool includes: a sampling head to sample the fluid, and a downhole fluid analysis module including a spectrometer capable of measuring a concentration of a surface active species in the fluid, and a processor configured to determine the IFT of the fluid downhole based on the measured concentration of the surface active species.

Other aspects and advantages of the claimed subject matter will be apparent from the following description and the appended claims.

BRIEF DESCRIPTION OF DRAWINGS

FIGS. 2.1 and 2.2 are illustrations showing Fourier transform infrared (FTIR) spectra for various samples of crude oil in accordance with embodiments of the present disclosure;

FIGS. 11.1 and 11.2 are illustrations of a multi-faceted prism for a dual path ATR spectrometer in accordance with embodiments of the present disclosure;

FIGS. 13.1 and 13.2 are illustrations of a multi-faceted prism for a dual measurement cell ATR spectrometer in accordance with embodiments of the present disclosure.

DETAILED DESCRIPTION

Figure 1:
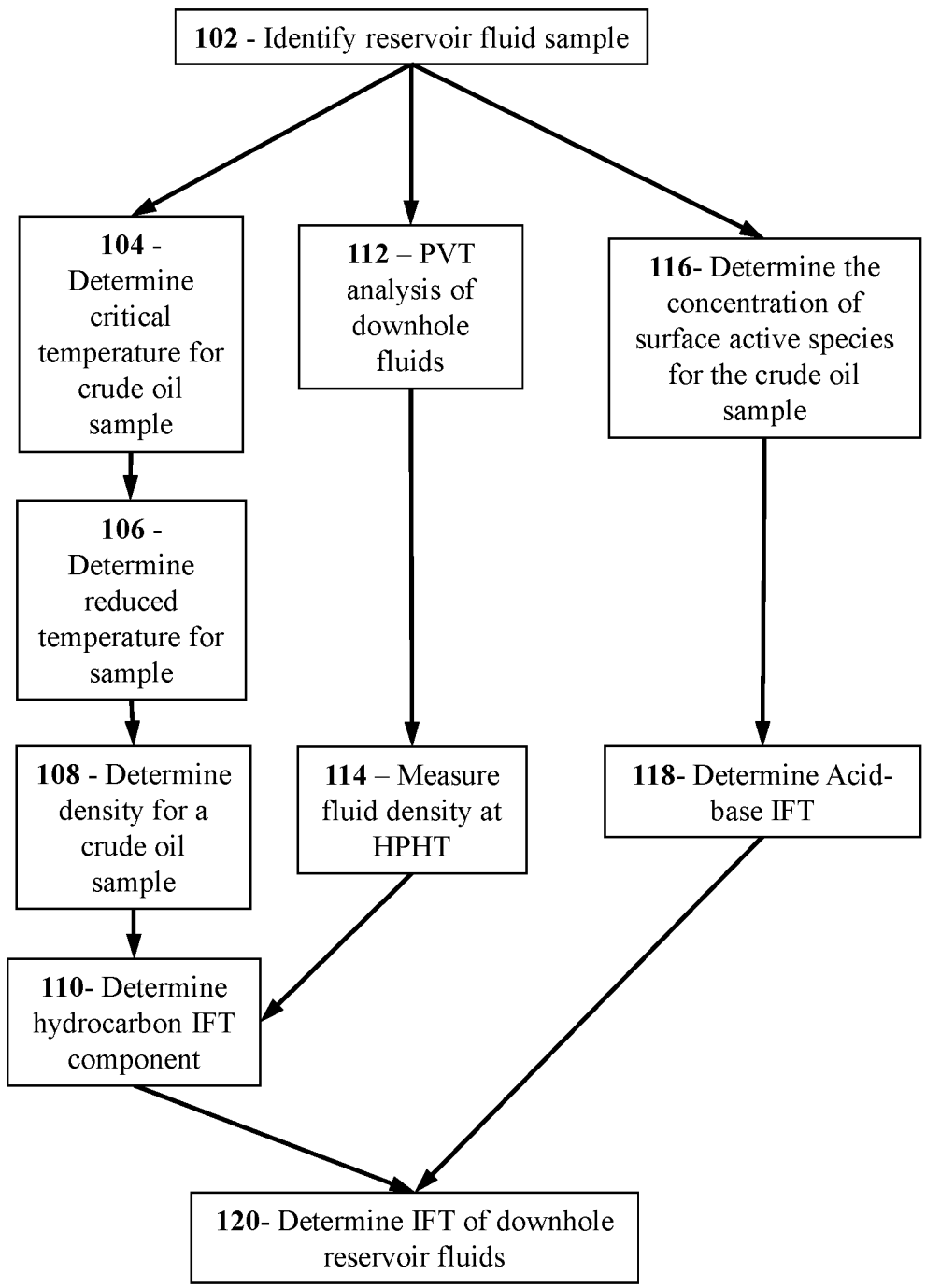
FIG. 1 is a flow diagram depicting a method in accordance with embodiments of the present disclosure.

In one aspect, embodiments disclosed herein relate to methods for predicting interfacial tension (IFT) in mixed fluid systems. Methods in accordance with the present disclosure may correlate an acid-base IFT from surface active species in a reservoir fluid to hydrocarbon IFT using a correlation of crude oil density and critical temperature to determine overall interfacial tension of a complex fluid mixture.

Methods in accordance with the present disclosure may be directed to the calculation of IFT downhole through the direct measurement of bulk fluid properties and the concentration of various surface-active species in situ. In one or more embodiments, methods include the measurement of surface active materials such as organic acids in crude oils sampled downhole using optical spectroscopy, electrochemistry, and/or colorimetric analysis. In some embodiments, methods may include the use of downhole tools configured to determine IFT for reservoir fluids at one or more depths and, based on measured acid content and density, may provide estimates for IFT of crude oil and hydrocarbons at other depths within a given well or formation.

Embodiments of the present disclosure may be directed to optical measurement tools for measuring fluid samples that include custom designed measurement cells for operation at high pressures and high temperatures that allow for control of path length and optical alignment. In one or more embodiments, a fluid inlet system may be used to control fluid flow into an optical measurement cell to optimize the measurement performance based on logging speed of a wellbore tool. In some embodiments, optical measurement systems may include an ATR spectrometer having resilience to external pressure, controllable sample window dimensions, and a modular design for ease of maintenance.

Mixed systems in accordance with the present disclosure may contain mixtures of aqueous and non-aqueous fluids, such as crude oil and other wellbore fluids, and mixtures of fluids and gases. In some embodiments, the IFT of a mixed system may be determined by calculating the sum of IFT contributions from the acid-base interactions at the interface between the phases, and the IFT contribution from the hydrocarbon or non-aqueous phase. The principle behind the assessment of IFT is through the relation of IFT and concentration of surface active species in the oil.

As shown in Eq. 1, the IFT γ of a multiphase mixture is the sum of the acid-base IFT $\gamma_{AB}$ and the hydrocarbon fluid IFT $\gamma_{HC}$, where $\gamma_{AB}$ is a function of the concentration of the surface-active species that may be described by suitable expressions for describing interfacial tension such as presented in Eq. 2.

$$\gamma = \gamma_{HC} + \gamma_{AB} \qquad \text{Eq. 1}$$

$$\gamma_{AB} = -RT\Gamma_m \ln(1 + K_L C) \qquad \text{Eq. 2}$$

In Eq. 2, R is the gas constant, T is the temperature of the sample, $\Gamma_m$ is the maximum adsorption at equilibrium, $K_L$ is the Langmuir adsorption equilibrium constant, and C is the bulk volume concentration of the surface-active species such as an organic acid or other surfactant. Note that $\Gamma_m$ and $K_L$ are empirical parameters that can vary over different crude oil samples. $K_L$ represents the strength at which the surface-active compounds bind to the interface and therefore is an indicator of the surface activity different from the surface or interfacial tension. Several different adsorption isotherms can be applied depending on the data available and the theory applied to the adsorption phenomenon.

In one or more embodiments, methods in accordance with the present disclosure may determine the $\gamma_{HC}$ and $\gamma_{AB}$ at downhole conditions by assessment of physical properties and the concentration of surface active species and estimate the IFT at reservoir conditions. While $\Gamma_m$ in Eq. 2 may be relatively constant, the equilibrium constant $K_L$ is a function of the solvent power of a given crude oil. $K_L$ can therefore be related to the properties of the oil, particularly the density and refractive index of the fluid. In an example, an increase in refractive index will result in a decrease in $K_L$, which may be regressed and corrected as a function of fluid composition across a reservoir in some embodiments.

Methods in accordance with the present disclosure may use direct and/or indirect determinations of the relative concentrations of various surface-active species and fundamental relationships to calculate IFT and surface adsorption in a downhole environment. Calculation of IFT from the concentration of surface active species is discussed, for example, in WO2016/018229 and U.S. Pat. Pubs. 2015/0114837 and 2015/0047979, which are incorporated herein by reference.

In one or more embodiments, methods of calculating IFT may include measuring an IFT for a control fluid without surface active agents and for fluids containing known concentrations of surface active agents to establish a calibration curve, followed by a measurement of the concentration of the surface-active species to determine the change in IFT. In some embodiments, baseline fluids may be generated by treating a crude oil sample with an adsorbent such as an ion exchange resin to separate surface-active species and obtain the baseline fluid. The surface-active species are then mixed with the baseline fluid in known quantities, to reconstruct the crude oil sample. These sample can be measured, as described in WO2016018229 A1, and the results used to generate a calibration curve or a look up table for use with samples having an unknown concentration of surface active species.

Methods in accordance with the present disclosure may include direct measurement of the content of surface active species at the surface or down hole, which may then be used to calculate IFT and surface adsorption. In some embodiments, surface active organic acids may be quantified using several suitable measurements, including by direct measurement of carbonyls by infrared spectroscopy using the full spectrum analysis or by using intervals such as in the 1750-1600 $cm^{-1}$ range. Other measurement techniques may include Raman spectroscopy, or colorimetric methods using chemical reagents that react with surface active species containing carboxylic acid groups, which are then detected by FTIR, Raman, UV-vis, vacuum-UV or fluorescence spectroscopy or by electrochemical measurements, or any combination of these.

In one or more embodiments, methods may include verifying the results obtained from downhole measurements, by comparing the results with measurements taken at surface conditions or at other positions within a wellbore. In some embodiments, a fluid sample obtained at a single depth may be used to improve or validate calculations of a concentration-IFT profile from a log measurement taken at any other depth within a reservoir.

Methods in accordance with the present disclosure may be used to determine the IFT for complex fluid systems using measurements obtained directly downhole. An overview of a method in accordance with the present disclosure is provided in FIG. 1, which discusses methods for determining the interfacial tension between any two fluid phases found in a formation by calculating the sum of the hydrocarbon IFT and the acid-base IFT. In one or more embodiments, methods of determining IFT may include real-time measurement techniques that monitor changes in IFT and wellbore composition during a wellbore operation using measurements taken above or below the surface.

At 102, a reservoir fluid having an unknown IFT is identified and sampled. The sampled reservoir fluid may be sampled using a wellbore tool and analyzed downhole or transferred to the surface for analysis. In one or more embodiments, the IFT is determined by measuring the hydrocarbon component $\gamma_{HC}$ and acid-base component $\gamma_{AB}$ of the IFT using Eq. 1 and determining the IFT gradients present, if any.

In order to calculate the IFT for the mixed fluid system, the contribution from the hydrocarbon/non-aqueous phase is calculated. At 104, the critical temperature of a hydrocarbon phase (such as crude oil) is calculated using a known concentration of hydrocarbons. At 106, the critical temperature of the sample is corrected and used to calculate the reduced temperature, while the densities of fluids are obtained at 108 by the measurement of a downhole tool as described below.

The fluid densities and the reduced temperature from 106 and 108 are then input into an equation to determine $\gamma_{HC}$ at 110, including, but not limited to, the Sutton equation Eq. 3, where $\rho_w$ and $\rho_h$ are the densities of water and hydrocarbon respectively. The reduced temperature $T_r$ is the ratio of operating temperature to a pseudo-critical temperature of the two fluids.

$$\gamma_{HC} = \left[\frac{1.58(\rho_w - \rho_h) + 1.76}{T_r^{0.3125}}\right]^4 \quad (3)$$

The pseudo critical temperature is the critical temperature of fluids corrected for the fact that the two liquids are not completely immiscible, and at equilibrium there is some oil in water and some water in oil. As a result, the critical temperature of the two-phase system is a weighted average of the critical temperatures of individual phases. Established methods can be used to calculate the pseudo-critical temperature and ultimately the reduced temperature.

In some embodiments, $\gamma_{HC}$ may be calculated by determining reduced temperature and/or critical temperature for a sample through pressure volume temperature (PVT) analysis or downhole fluid analysis (DFA), in addition to determining fluid density at high pressure and high temperature (HPHT). For example, a PVT analysis 112 may be used in some embodiments to determine a reduced temperature of a fluid sample, while density of the fluid at HPHT is determined at 114. The determined density and reduced temperature for the samples may then be converted to $\gamma_{HC}$ at 110, using a suitable equation such as the Sutton equation at Eq. 3.

At 116, the acid-base IFT $\gamma_{AB}$ is determined from a concentration of surface active species, such as organic acids and other surfactants, quantified by one or more spectroscopic techniques. The $\gamma_{AB}$ is calculated using an isotherm such as that described in Eq. 2 and correlations of $K_L$ and $\Gamma_m$, or any other known adsorption isotherm constants. In some embodiments, the calculated $K_L$ and $\Gamma_m$ values may be modified using relations between refractive index and oil properties and the impact of fluid properties variations on these parameters. In one or more embodiments, spectroscopic techniques to calculate the concentration of acids in a sample may include optical spectroscopy such as infrared (IR), Raman scattering, UV-vis, and the like, colorimetric methods, electrochemistry, and other techniques capable of detecting carbonyl-containing species.

In some embodiments, determining the acid concentration at 116 for a sample may be determined using colorimetric analysis. During colorimetric analysis, acid is neutralized and the generated heat of reaction is used to calculate the concentration of the surface-active species. The value of $\gamma_{AB}$ and Eq. 2 may then be used to calculate the acid-base interfacial tension component of the fluid mixture. The values for $\gamma_{HC}$ at 110 and $\gamma_{AB}$ at 118 may then be combined at 120 to determine the bulk fluid IFT for the mixed fluid system.

In one or more embodiments, the concentration of surface active species may be measured at a plurality of depths using the same calibration curve (look up table) for each depth to determine $\gamma_{AB}$ at each depth. In some embodiments, these results can be combined with $\gamma_{HC}$ to determine a log of interfacial tension as a function of depth.

Methods in accordance with the present disclosure may incorporate direct detection and quantification of organic acids using various IR-based detection techniques. Direct spectroscopic detection methods are aided by the selection of absorption lines for analytes that have limited interference from other components in a sample. For surface active species such as organic acids, the absorption line for carbonyl carbon (C═O) is approximately 1718 $cm^{-1}$ in the IR spectra. Within an IR spectra, using the carbonyl absorption line as a proxy enables the concentration of surface active species to be determined accurately because there is a substantial window between ~1700-2200 $cm^{-1}$ in which no other absorption features exist in most samples of downhole fluids and crude oil.

As shown in the crude oil sample in FIGS. 2.1 and 2.2, the lack of competing signals in this IR range permits measurement without interference by other components in the fluid. For crude oils, the range of 1800-2200 $cm^{-1}$ provides no absorption and can be used for background subtraction. The IR spectrum in the entire range, or in the limited range of 1600-2200 $cm^{-1}$, provides the needed data to calculate a normalized absorption due to C═O stretch line corrected for background from which the concentration of surface active species can be calculated. With respect to FIG. 2.1, a wide range IR spectra is shown for a crude oil sample, while FIG. 2.2 is a subset of the spectra between 1900 and 1500 $cm^{-1}$. Peaks at 1750 to 1700 $cm^1$ relate to carbonyl vibrations, while the peak around 1600 $cm^{-1}$ is assigned to aromatic C═C stretch.

In one or more embodiments, IR measurements may include through-path or attenuated total reflection (ATR) methods, which may be combined with a reference measurement to minimize the effect of any common-mode measurement degradations, such as source drift, or fouling on the optical cell windows.

In one or more embodiments, surface active species may be quantified by measuring carboxylic acid concentration using optical measurements on a baseline crude oil (such as an acid-free crude oil) and an original crude oil.

Optical techniques in accordance with the present disclosure may include passive optical techniques that allow non-contact measurement of the species within a fluid, which minimize measurement interference from the addition of analytes or fluid losses to purification and separation techniques. For example, IR-based optical techniques may be used to determine the concentration of organic acids and other carbonyl containing surface active agents.

In one or more embodiments, methods may utilize a downhole tool containing a downhole fluid analysis (DFA) module configured to obtain the measurements required to determine IFT for a fluid downhole. With respect to FIG. 3, an embodiment of a downhole tool 300 is shown in a borehole 302 drilled in the earth formation 304. The figure is provided for illustration of a general downhole fluids sampling device, and not intended to convey specific scale or mandatory component configurations.

In one or more embodiments, downhole tool 300 may be conveyed using a wireline cable 306, and may further contain other tools and components such as wireline formation sampling tools, production logging tools, logging while drilling or measurement while drilling (LWD/MWD) sampling tools, coil tubing sampling tools, downhole fluid analysis tools, or any other downhole formation sampling tool known to those of ordinary skill in the art. Further, while a fluid sampling tool 300 is shown emplaced and retrieved by wireline, the systems, devices, and methods of the present disclosure may also be configured as permanent or semi-permanent downhole monitoring applications.

Wireline cable 306 may provide electrical power for the operation of tool 300, perform data telemetry, and provide commands to control the tool operation. The downhole tool may include several standoffs 308 and several modules that are operationally connected and are disposed within a housing or drill collar. These modules may include a sampling module 310, a control module 312, a pumping module 314, an electronics and telemetry module 316, fluid monitoring module 318, and a downhole fluid analysis module 320. It is to be understood that the fluid monitoring module 318 and the downhole fluid analysis module 320 are not essential for extracting formation fluid and may be distinct tools, part of a downhole tool string, and capable of operating independently. In one or more embodiments, fluid monitoring module 318 and the downhole fluid analysis module 320 may receive a formation fluid provided by a sampling module 310, and perform their own specialized measurements as independent tools rather than as modules.

At a particular depth, the sampling module 310 activates a probe-head that forms a hydraulic seal with a wall of the borehole, and draws the formation fluid into the sampling module 310. In some embodiments, the drawn fluid may be a mixture of connate fluid and the mud filtrate from the invaded zone, and fluid may continue to be collected until the drawn fluid is composed of substantially the connate fluid for analysis.

The drawn fluid may pass from the sampling module 310 into fluid monitoring module 318. Fluid monitoring module 318 may include one or more sensors capable of measuring various physical parameters of the fluid such as, but not limited to, resistivity, dielectric permittivity, refractive index, temperature, density, and/or viscosity. In some embodiments, fluid monitoring module 318 may incorporate a vibrating sensor to measure fluid density, which is available commercially by SCHLUMBERGER™. During operation, a vibrating sensor may collect a fluid in an internal chamber where a spring is vibrating in two modes. The resonance frequencies of these vibrations depend on the density of fluid in which the spring is immersed in. A measurement of the resonance frequencies provide input to a physical model describing the resonance frequencies and quality factors of the sensor and is solved to back out the fluid density. The density measurement can be provided by a vibrating sensor as discussed in this example, or any other method known in the art for obtaining density measurements downhole.

Figure 3:
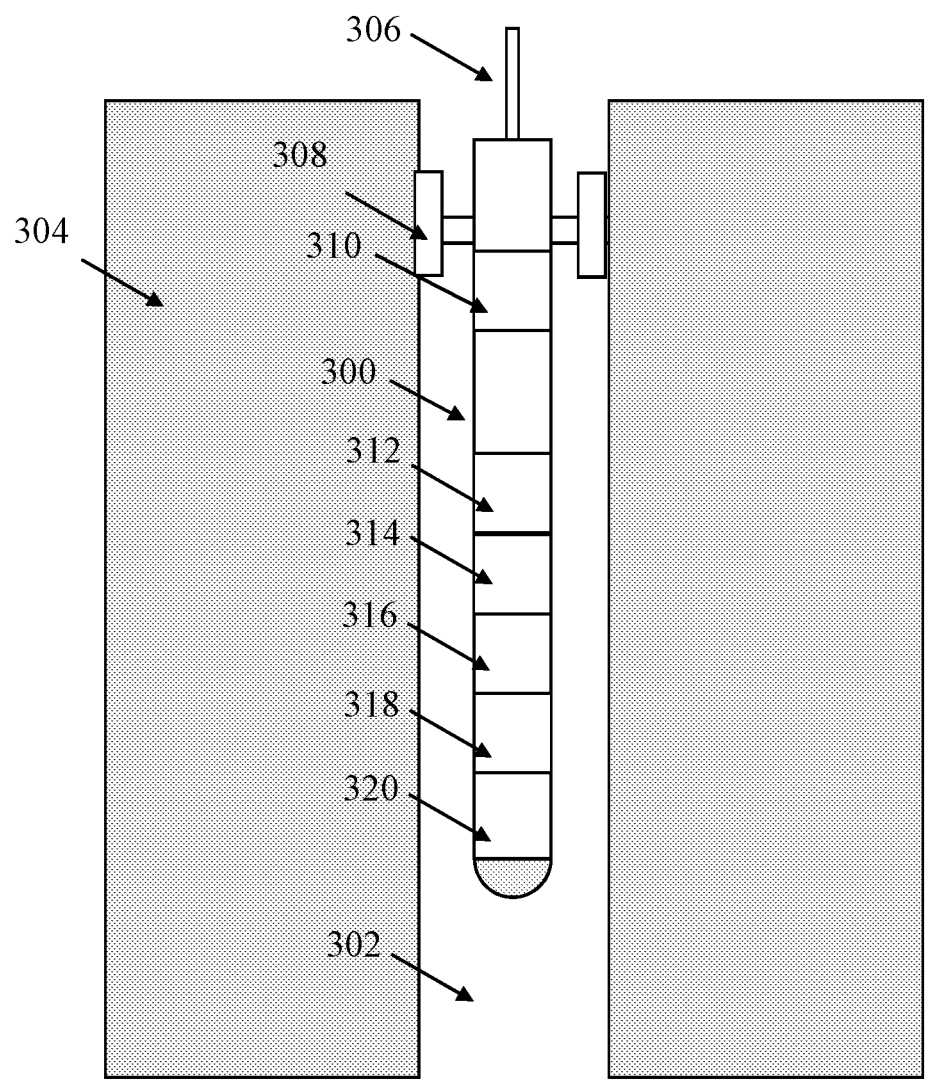
FIG. 3 is an illustration of a wellbore tool for measuring interfacial tension in accordance with embodiments of the present disclosure.
Figure 4:
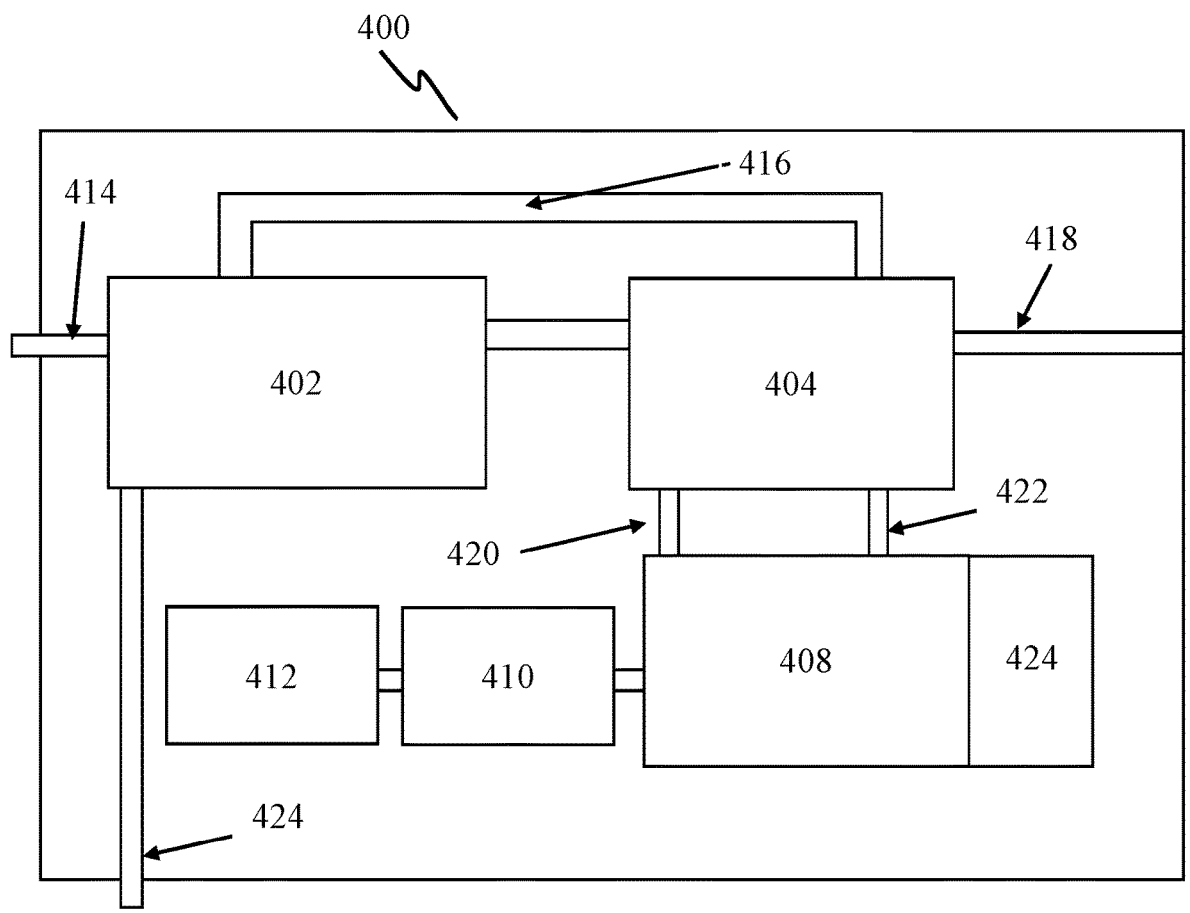
FIG. 4 is a schematic of a spectroscopic system in accordance with embodiments of the present disclosure.

After processing in fluid monitoring module 318, a sample fluid may then be transferred to downhole fluid analysis (DFA) module 320, where chemical and/or physical analyses are performed on the fluid while the tool 300 is disposed within the wellbore 302. With respect to FIG. 4, an example component arrangement of a DFA module 320 from FIG. 3 is shown at 400. DFA module 400 may include a spectrometer 404 that performs optical measurements or alternate types of spectral measurements on the fluid sample to infer concentrations of constituents and/or other chemical or physical properties of the components of a sampled formation fluid. In some embodiments, measurements obtained from formation samples may be made in substantially real-time and on samples taken from various locations during a single trip of the tool 300 in the wellbore 302. The spectrometer 404 can also be deployed as part of a permanent completion within the wellbore in some embodiments. The spectrometer 404 can be deployed by any means known to those ordinarily skilled in the art and is not intended to be limited to the exemplary methods described herein.

"Spectrometer" as used herein will also generally refer to the device within the downhole fluid analysis module 400, and it should be recognized that this term is not being used to refer to a particular type of spectral evaluation device, but is intended to refer generally to a class of devices used in conjunction with the evaluation, or analysis of spectra obtained from the interaction of electromagnetic wave of different frequencies with the sample and may be in well-known bands such as visible, infrared, and ultraviolet. The spectrometer can be used in any kind of spectroscopy monitoring including, but not limited to, optical monitoring, spectrophotometry, spectrofluorometry, spectrum analysis, or spectrocolorimetry.

In one or more embodiments, spectrometer 404 includes optical components to shape, manipulate, or route incident electromagnetic wave (light) of certain frequency range to targets of interest, spectrally disperse incoming light, image the dispersed light onto a spatial, spectral, or temporal filtering device, direct the filtered light onto, into, or around (bypassing) a sample, and then direct the light to some type of optical detector. In some embodiments, spectrometer 404 may also include multiple detectors.

The spectrometer 404 may be controlled by a processor disposed within the fluid analysis module 400. In one embodiment, commands can be preprogrammed in the processor so as it can operate autonomously or semi-autonomously. Alternately, commands can be input from the surface in real time such as via the previously discussed telemetry system. The processor controls the operation of the spectrometer 404 and, in another embodiment, can be used in processing results obtained from the spectrometer's response to fluids.

In one or more embodiments, the fluid analysis module 400 receives fluid from the inlet port 414 and discards analyzed fluids through outlet port 418. In some embodiments, subcomponent 402 may perform downhole fluid analysis, including determinations such as density, temperature, reduced temperature, critical temperature, phase information, and the like. Subcomponent 402 may also contain the hardware, processor, and software needed to perform the fluid analysis. Measurements performed in subcomponent 402 include non-destructive optical measurements such as visible, infrared, and near infrared absorption measurements. In embodiments in which destructive analytical techniques are performed, sample fluid is prevented from continuing to the spectrometer 404 and is instead discarded through port 424 and the spectrometer 404 is provided with the fluid through the by-pass line 416.

In embodiments in which non-destructive analysis is performed at 402, the fluid may continue to the spectrometer 404. The downhole fluid analyzer 400 may also contain a subcomponent 408 in fluid communication with the spectrometer 404 that functions to modify the sample fluid, such as when combining the sample fluid with various reagents.

In one or more embodiments, downhole fluid analyzer 400 is designed to use a spectrometer 404 to make direct measurements on the downhole fluids extracted from the formation. In some embodiments, a reagent chemical may be reacted with a sample fluid prior to analysis to produce a chemical indicator that may be measured using the spectrometer 404. Combination of a reagent with a sample fluid may be performed by directing the sample fluid through port 420 to mixing chamber 408, which may be a tank or other vessel, and contacting the sample fluid with a chemical reagent delivered from tank 412 to 408 using a suitable delivery mechanism, such as a micropipette 410. A mixing mechanism 424 for combining the reagent and sample fluid may be disposed in or on mixing chamber 408. Mixing mechanism 424 may be any suitable mechanism for mixing fluid samples, including a magnetic stirrer, a mechanical stirrer, or an ultrasonic transducer, and the like. Following sample mixture, the sample may be transferred back to spectrometer 404 through port 422 for analysis of any resulting chemical indicator.

In one or more embodiments, spectrometer 404 may operate in the infrared (IR) spectral range. In some embodiments, IR spectrometers may include attenuated total reflection (ATR) and through-path absorption spectrometers. Methods in accordance with the present disclosure may use a reference measurement (which may be corrected for background noise) that minimizes the effect of any common-mode degradations, such as light source drift, fouling on the optical cell windows, and purity of the absorption band, and the like.

Spectrometers in accordance with the present disclosure may be broken down into a number of elements that are discussed in turn below. In one or more embodiments, spectrometers may include at least three components: an optical source, a sample cell, and a detection system. Components may be configured to operate in the IR range and/or other ranges such as visible and ultraviolet.

Methods in accordance with the present disclosure may utilize a downhole tool incorporating one or more optical sources. In one or more embodiments, optical sources may include narrow linewidth sources such as quantum cascade laser diodes, external cavity quantum cascade lasers, superluminescent diodes, and the like. Narrow linewidth sources may have higher brightness and directionality, which is advantageous in downhole applications. Narrow linewidth sources also operate at controlled wavelengths that can eliminate the need for an external spectrometer to discriminate the attenuation of a specific absorption line. However, there are challenges with operating some optical sources at elevated temperatures such as quantum cascade lasers, and the addition of an external cavity to optical sources can create design issues with mechanical and thermal stability under downhole conditions.

In one or more embodiments, optical measurements by narrow linewidth sources may be performed using a single wavelength through the measurement path and a reference path that is not exposed to the hydrocarbon, or a differential path length which are both exposed to the hydrocarbon. In some embodiments, optical measurements may incorporate at least two wavelengths. For example, an optical setup may incorporate two wavelengths selected for high and low attenuation of the target species, which may allow for signal correction for scattering effects and utilization of the full optical beampath of the measurement path.

In one or more embodiments, optical sources may include broadband sources such as blackbody IR sources. Blackbody IR sources may be cost-effective, spectrally continuous, compact, and rugged. In some embodiments, blackbody IR sources may be modulated to produce a signal for lock-in detection, and may include optics such as calcium fluoride or zinc selenide lenses to optimize the beam structure. However, use of a blackbody IR source may require some form of spectral discrimination within the system.

Methods in accordance with the present disclosure may utilize a spectrometer that enables analysis of a portion of a broadband emission by wavelength (frequency) for detection. A number of suitable spectrometers are discussed below.

Spectrometers in accordance with the present disclosure may include a grating spectrometer capable of a controllable reduction in spectral width from a broadband source. Grating spectrometers may either be fixed where the spectral content of a particular beampath does not require changing, or variable, where the spectral content of the particular beampath can be tuned by altering the incidence or exit angle of the grating with respect to the beampath, using the standard equations which are well-known in the field. The fixed implementation tends to offer higher robustness compared to a tunable version due to the elimination of moving parts.

In one or more embodiments, wavelength selection may include the use of a Fourier transform spectrometer. The resolution of the spectrometer is inversely proportional to the displacement of the mirror. For example, a mirror displacement of 100 µm in a Michelson interferometer yields a resolution of approximately 50 $cm^{-1}$, which allows separation between the absorption lines of the C=O stretch and nearby competing lines and the reference region of the spectrum.

Figure 5:
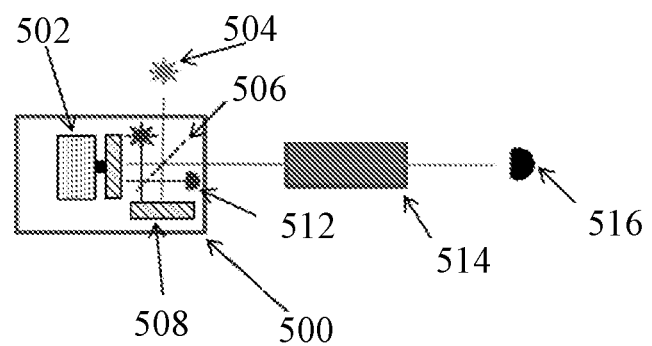
FIG. 5 is a schematic of a Fourier transform spectrometer in accordance with the present disclosure.

With respect to FIG. 5, an example of a Fourier transform infrared (FTIR) spectrometer in accordance with the present disclosure is shown. During measurements, a light source 504 provides a beam that enters the FTIR system 500, which contacts beamsplitter 506. Radiation incident on the beamsplitter is divided into two beams. The first beam is transmitted through the beamsplitter 506 to the fixed mirror 508 and the second is reflected off the beam splitter 506 to the moving mirror 502. The fixed mirror 508 and moving mirror 502 reflect the radiation back to the beamsplitter, with the result that one beam passes through measurement cell 514 and to detector 516 to generate an interferogram.

In one or more embodiments, spectrometers may utilize a piezo-electric stack 502 for mirror displacement, which permits rapid scanning to produce an averaged result, yet retains a mechanically resilient construction. The spectrometer can be situated at any point between the source 504 and detector 516. Conversion of the captured interferogram to spectral content can be achieved using a few different methods. FTIR systems may also include a separate calibration system that use a visible laser and calibration detector 512 to verify mirror 502 displacement and the corresponding spectral measurements.

Spectrometers in accordance with the present disclosure may include interference filters (thin-film dichroics), which are a compact, low-cost and robust way of producing a very wide variety of transmission spectra. Interference filters in accordance with the present disclosure may also be present on mirrors and other optical surfaces in a downhole analyzer to reduce (Fresnel reflections) optical losses in the beampath and the amount of stray light in the system which may reduce the system performance.

In one or more embodiments, spectrometers may also incorporate one or more absorption filters to provide coarse filtering to the spectral content of a broadband source.

A reference measurement that compensates for beampath variations improves the accuracy of the absorption measurement. While this reference measurement does not need to use the same beam-path, optimal rejection of deleterious effects is achieved when the overlap between the reference and measurement optical paths is maximized. These effects include: misalignment of optical components (for example caused by shock, temperature or vibration), degradation of the transmission of optical components (for example by chemical attack on the measurement cell windows), variation in the source characteristics (for example spatial or temporal fluctuations of the intensity or wavelength characteristics from ageing effects), and variation in the detector sensitivity and so forth.

Datasets show that crude oils have a low absorption (high transmission) in the region between 1800-2400 $cm^{-1}$, which may allow the same source, detector, and passive components used to measure sample analytes to be employed to compute a baseline condition for the optical chain.

In one or more embodiments, methods of measuring the concentration of surface active species in a sample such as organic acids may include the use of solid phase chromatography materials. Methods utilizing solid phase approaches may include pumping a fluid sample through a column of an adsorbent at downhole conditions to isolate or reduce the concentration of surface active species. In some embodiments, the concentration of surface active species may be determined by measuring a first concentration of surface active species entering the column and calculating the differential of the concentration leaving the column.

Optical measurements of surface active species may be obtained using several configurations. While a number of example configurations are introduced, it is envisioned that any configuration that exhibits a proportional response to increasing concentration of surface active species may be used.

In one or more embodiments, a grating or FTIR spectroscopic system may be used to capture both the measurement and reference part of the spectrum. An example of this implementation is shown in FIG. 5. Note that the spectrometer can appear anywhere in the optical path, and need not follow immediately after the source.

In one or more embodiments, alternating optical filters in a single beampath may be used to selectively expose a detector to measurement and reference wavelength regions to the optical system. For example, an alternating filter system may involve a rotating disc containing a known number of the filters in front of the source or detector. In this way, the optical path of the system is measured alternately at the measurement and reference wavelengths using the same components and beampath. This also serves the purpose of providing a "lock-in" frequency (in optical terms it "chops" the signal) that can be used to further narrow the signal bandwith and improve the signal to noise ratio.

Figure 6:
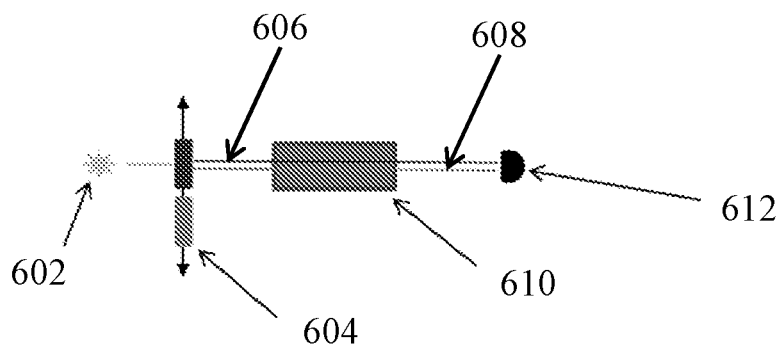
FIG. 6 is a single path implementation of a spectroscopic system using alternating filters in accordance with embodiments of the present disclosure.

With respect to FIG. 6, an implementation of a spectrometer configured with alternating filter sets is shown. Source illumination 602 passes through an optical filter switching system (chopper) 604, creating a measurement illumination path 606 and a reference illumination path 608, depending on what filter set is the beampath. The illumination paths 606 and 608 are configured to pass through measurement cell 610, where the absorption of the sample measured by detector 612. Note that the filters can be anywhere within the measurement system, and do not need to immediately follow the optical source.

In one or more embodiments, spectrometers may incorporate multiple beampaths. Optical configurations using multiple beampaths utilize optical trains having a high degree of commonality but with fixed filters to select the wavelength of light propagating in each. Multiple beampaths may be used when there is a desire to eliminate moving parts associated with changing filters in the signal path, or where the chopping of the signal results in unacceptable dead-time in the measurement.

Figure 7:
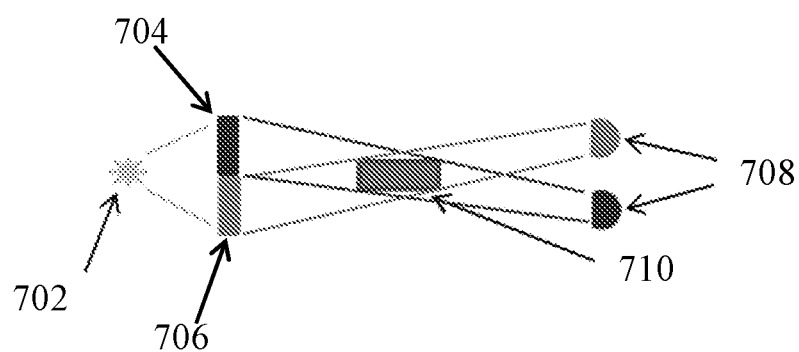
FIG. 7 is a schematic of an implementation of a measurement system utilizing fixed filters on two beampaths with two wavelengths, through a single measurement cell, using two detectors, and no moving parts in accordance with embodiments of the present disclosure.

With respect to FIG. 7, a dual beam path setup is shown. A single illumination source 702 is used to illuminate both a reference illumination beampath 704 and a measurement illumination beampath 706. Each beampath traverses the measurement cell 710 and focuses on a corresponding detector 708. In practice, this method may be done using separated pathways to maintain a common source (and spectrometer system where used), and while this requires two detectors and digitization systems, there is a tradeoff of improved mechanical and thermal stability by removing mechanical parts from the system.

Figure 8:
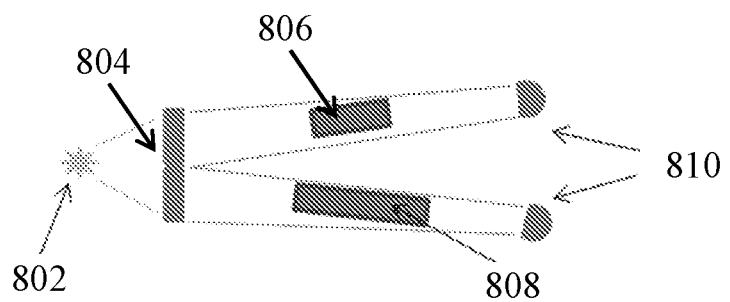
FIG. 8 is a schematic of an implementation of a multi-cell measurement system, using a single spectrum of wavelengths, and two detectors in accordance with embodiments of the present disclosure.

In one or more embodiments, optical configurations may include the use of single source illumination multiple measurement cells of differing attenuation, which may provide a differential measurement of attenuation at the measurement wavelength. With respect to FIG. 8, an optical configuration having multiple measurement cells is shown. Illumination source 802, passes through optical filters 804, creating two beampaths. Each beampath passes through a measurement cell 806 and 808 having different cell length and will attenuate incident illumination to differing degrees. Illumination passing through measurement cells 806 and 808 is then registered by detectors 810.

In all optical configurations, the design of the detectors may be selected depending on the conditions in a selected operating region and require careful attention for the selected operating region. In one or more embodiments, a detector, such as an indium antimonide (InSb) or mercury cadmium telluride (HgCdTe or MCT), may be employed in combination with a cooling device such as a Peltier device. In some embodiments, heat-sensitive detectors may also be configured to operate within a vacuum to minimize heat conduction to the sensing elements of the detector.

At high operating temperatures, it may not be practical to utilize heat-sensitive detectors, in which case thermopile or photo-acoustic detection may be employed alone or in combination with optical lock-in detection. Where a scanning spectrometer is used, the detector bandwidth and the spectrometer scanning frequency may be co-designed to maximize the system performance. The performance of a detection system can also be enhanced with optical "lock-in" detection in which the source is modulated to remove effects associated with drifts and electrical interference effects. Where a tuned grating or FTIR spectroscopic system is employed as the wavelength discrimination, modulation of the source may be above the bandwidth required for the spectroscopic measurement.

Methods in accordance with the present disclosure may utilize optical configurations that incorporate one or more measurement cells. A variety of approaches can be taken with regard to the design of the measurement cell. In one or more embodiments, measurement cells may be designed to withstand pressures, temperatures, and chemistry of the downhole environment.

Measurement cells in accordance with the present disclosure include windows formed from materials having low attenuation in the spectral region of interest, mechanical resiliency, and chemical resistance. Chemical resistance may be important where the downhole environment can involve contact with chemicals under high temperature and high pressure, and may be highly corrosive or acidic. Because of harsh operating conditions, measurement cells may be designed to be simple, field-operable servicing/replacement of the optical cell structure with alignment "by design" rather than employing mechanical elements that may be prone to calibration errors.

Measurement cells in accordance with the present disclosure may be prepared from materials such as those described below.

Sapphire: Chemically and mechanically very resistant, but may have some absorbance in spectral regions of interest for crude oils. Designs incorporating sapphire measurement cells may utilize a short beam-path (~mm) to minimize signal attenuation.

Calcium fluoride: Excellent transmission in the relevant intervals, but may be mechanically weak. Exhibits low solubility in water, even at up to 150° C.

Germanium: Excellent transmission in the relevant intervals and good mechanical characteristics, exhibits both hardness and strength. High refractive index generates reflective losses at interfaces. Very low solubility in water.

Zinc Selenide: Classic material for MIR operation. Relatively soft, but with higher elastic limit than calcium fluoride.

In one or more embodiments, measurement cells may be categorized as two basic types, and both can operate on either the exterior of the tool, or by drawing a hydrocarbon sample into the interior of the tool. In both methods, an example will be provided for the exterior measurement, while the designs may also be adapted to function within the interior of a tool. In one or more embodiments, measurement cells may incorporate fluid inlet paths that draw fluids into the cell at stationary to low emplacement speeds, and to clean the cell at higher tool speeds. In some embodiments, inlet paths may be adjustable to control fluid access over a wide range of viscosity and fluid density.

In one or more embodiments, methods may include the direct measurement of surface active species using instruments configured to measure direct transmission of a sample. Direct transmission methods measure the amount of light that traverses a known length of the sample. In direct transmission measurements, a beampath is configured to pass through a known sample length and subsequently the intensity of light is measured and compared with the intensity of the beam before it passed through the sample. The ratio of these two intensities is used to calculate absorbance which is related to the characteristics of the sample through Beer Lambert relationship.

The length of sample is included within the system design to ensure that sufficient light reaches the detectors to enable the desired measurement. Where the absorption of the sample is variable, a system may include multiple, separate measurements of different sample length to increase the system dynamic range, and select between them using a predetermined criteria that optimizes the measurement for a given oil under investigation. A key limitation of the direct transmission system is that the optical attenuation of crude oils, and crude oil/water mixtures can be extremely high, requiring very short path lengths to effect a measurement, which in-turn become susceptible to blockage.

Figure 9:
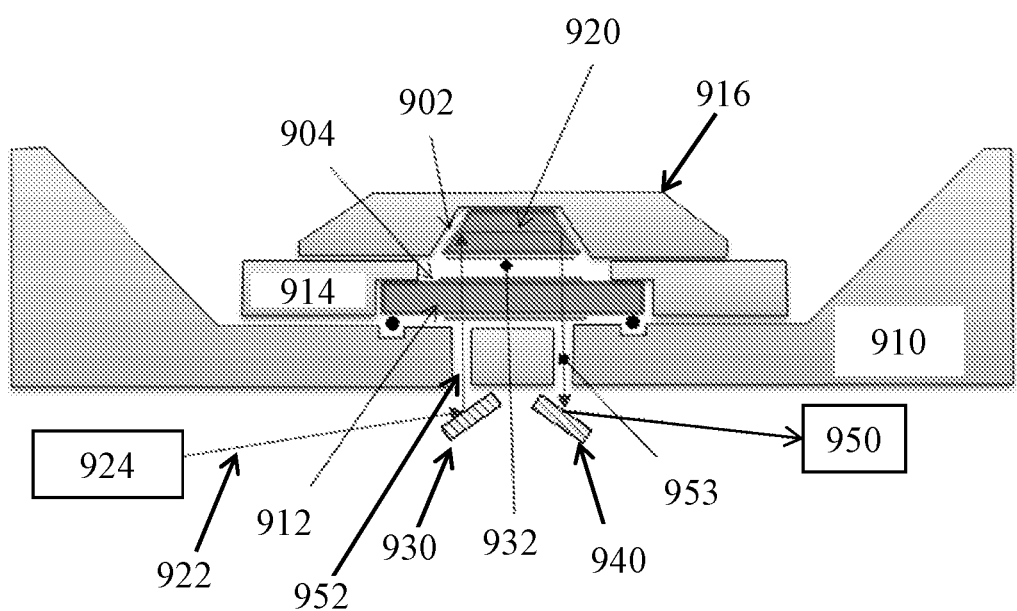
FIG. 9 is an example of a single-path transmission cell in accordance with embodiments of the present disclosure.

An example implementation with a single optical path length is shown in cross-section in FIG. 9. The metallic tool body 910 forms a base for the window 912 to be hydraulically sealed to and held in place by a metallic seal cap 914. In one or more embodiments, a seal may be formed by an o-ring and a metal to optical element "soldered" seal can be used to hold the seal cap 914 and the window 912 together. The seal is designed to protect the electronic and optical components from being flooded by the fluid samples. Above the seal cap 914, there exists a top cap 916 having a recess wherein a retro-reflecting prism 920 resides. There is a gap between the top of window 912 and bottom of the retro-reflecting prism 920 which serves as a sample chamber 932 through which a sample is transported and measured. An infrared beam 922 originates from the light source 924 and is reflected into the cell by a mirror 930. The beam 922 is perpendicular to the face of window 912 to minimize the light reflection. In some embodiments, the faces of window 912 may be coated with an antireflection coating to provide additional reflection suppression.

During measurement, beam 922 may pass through a sample contained in the sample chamber 932 and reaches the retro-reflecting prism 920. The two sides of prism 920 are cut at proper angles to ensure the light becomes internally reflected back toward the sample chamber 932. The reflected beam 922 passes through the sample and window again, reaching the second mirror 940 which directs the beam 922 to the detector 950. In some embodiments, Mirrors 930 and 940 can be formed from a single-piece of cut and coated material, for example glass, to make them more resilient and self-aligning.

In one or more embodiments, window 912 is completely supported by the metallic tool body 910 except for two orifices 952 and 953, which have diameters slightly larger than the diameter of the light beam 922. Because the total area of the two orifices 952 and 953 is smaller than the surface area of the window 912, there is little stress on the window 912 and it can readily withstand high pressures. In one or more embodiments, the retro-reflecting prism 920 and the sample chamber 932 are protected from mechanical damage by recessing them into the body of the external top cap 916. The top cap 916 can be removed to clean the sample chamber 932 and surfaces of the retro-reflecting prism 920. In some embodiments, prism 920 and window 912 may be coated with a reflective or dichroic coatings 902 and 904, respectively.

In FIG. 9, a cell spacer to control the optical path length is not shown for clarity. Contact regions between structural elements, such as those between metal and the optical components, may be coated with a polymer to minimize potential for failure from sharp points in some embodiments.

In one or more embodiments, the exterior optical path is protected from mechanical damage by either recessing it into the body of a downhole tool, or by an external protection element. In some embodiments, exterior retro-reflecting prism 920 may be fixed to the window 912 using an element that accurately controls the length of the optical cell exposed to the fluid and with features to effect automatic optical alignment. The retro-reflecting prism 920 may be attached to the tool body using frangible fixings, such that impact above a predefined threshold releases this prism 920 without compromising the pressure integrity of the optical window 912 into the tool. The retro-reflective element 920 can also be removed to facilitate cleaning of the optical surfaces in some embodiments.

In one or more embodiments, direct transmission measurements to determine IFT in accordance with the present disclosure may be obtained on a formation fluid sample using an in-situ fluid analyzer (IFA) commercially available from SCHLUMBERGER™. IFA is a high resolution optical analyzer (20+16 (grated on HC) channels), which may include comprehensive measurements of fluid properties with more accurate compositions (C1, C2, C3-C5, C6+, CO2) with higher resolution optical density channels, including measurements such as gas/oil ratio (GOR), gas/condensate ratio (GCR), density, viscosity, pH, resistivity, calibrated fluorescence (for multi-well and fluid variations), and pressure.

In one or more embodiments, methods may include the direct measurement of surface active species using instruments configured to measure attenuated total reflectance (ATR) of a sample. Methods incorporating ATR couple the evanescent field generated from total internal reflection within a prism to a sample contacting the surface of the prism. The sample attenuation can be very large at the interrogation wavelength, and the interaction length can be tuned to match this by changing the dimensions of the prism, and the incidence angle of the incoming beam. This approach typically employs materials with high refractive index at the wavelengths of interest, such as germanium, or zinc selenide.

Figure 10:
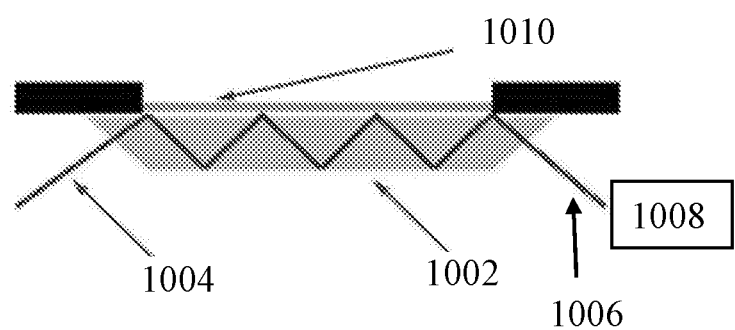
FIG. 10 is an implementation of an attenuated total reflectance (ATR) measurement in accordance with embodiments of the present disclosure.

With respect to FIG. 10, an example image of an ATR implementation is shown. The optical medium is a trapezoidal prism 1002. The incident beam enters the prism 1002 from one of the cut faces 1004 and reflects back and forth between the two flat faces of the prism 1002 at multiple locations, while staying in the prism, before it reaches the opposite end of the prism 1006 and exits toward the detector 1008. Every time the light beam reflects from the upper face, which is in contact with the sample 1010, there is an interaction between the light and sample.

The number of internal reflections can be varied by changing the angle of incident of the light. In one or more embodiments, the sample is crude oil and its absorption at the interrogation frequencies is dependent on the density of the oil. The ATR design enables the extent of light-sample interaction to be adjusted for optimum detectable signal by changing the incidence angle of the incoming beam. In some embodiments, ATR-based methods may employ prism materials with high refractive index at the frequencies of interest, such as germanium, or zinc selenide.

In one or more embodiments, ATR spectrometers may include multi-faceted prisms having facets designed according to Snell's law to split an incoming collimated beam into multiple beam paths, in a configuration similar to that described above with respect to FIG. 7 or FIG. 8. An implementation of the beampath configuration shown in FIG. 7, is shown in the multi-faceted prism design for an ATR spectrometer detailed in FIGS. 11.1 and 11.2. FIGS. 11.1 and 11.2 illustrate a dual path optical ATR system configured to measure a single measurement chamber at a measurement and a reference wavelength without mechanical deflectors, or chopping elements. With respect to FIG. 11.1, the multi-faceted prism includes multiple facets 1102 and 1104 on the light incident side, which divides incident light into multiple beampaths, such as a measurement path and reference path.

The angle of the facets 1102 and 1104 are designed according to Snell's law to split an incoming collimated beam into two ATR paths within the same prism, propagating across the measurement window in two different directions. These two beams reach the back facets 1106 and 1108 respectively, and are then directed to two separate detectors (not shown). Filters are shown on both the entrance and exit faces of the structure, which may be thin-film filters or dichroics designed to select the measurement and reference frequency ranges. In some embodiments, filters may be present on both the entrance and exit faces. In some embodiments, a first facet may include a single filter or dichroic, while the exit facet employs an anti-reflection coating instead.

The prism may employ an optical guidance enhancement layer 1110 which has a lower refractive index in the spectral region of interest than the base optical prism material. For example, in the case of a germanium prism, the enhancement layer 1110 could be a layer of GeO2. As a result, the oxide layer may act as a guide and serves to limit access of the evanescent wave to the sample chamber. In one or more embodiments, a sensing window may be etched into the enhancement layer 1110 that is defined and matched to the system performance requirements, while the physical structure of the prism can be optimized for the mechanical arrangement, such as detector separation and mechanical resistance to pressure. The enhancement layer 1110 may allow seals to be placed on the front face of the structure, preventing access of fluids to the interior of the tool and preventing adhesives and sealing components from interfering with the optical measurements.

With respect to 11.2, the thickness of guidance enhancement layer 1110 renders the back face of prism uneven. To ensure this is not interfering with the prism's performance and mechanical strength, a layer of absorbing material 1114 deposited onto the back face of the prism and selectively patterned to cover the area not covered by the guidance layer 1110. The material used to make layer 1114 may be chosen to control the stray light in some embodiments. As an example, in the case of a germanium ATR prism, and a measurement in the mid-infrared, a thin film of aluminum may be used and patterned using photolithographic or spray masking techniques.

Figure 12:
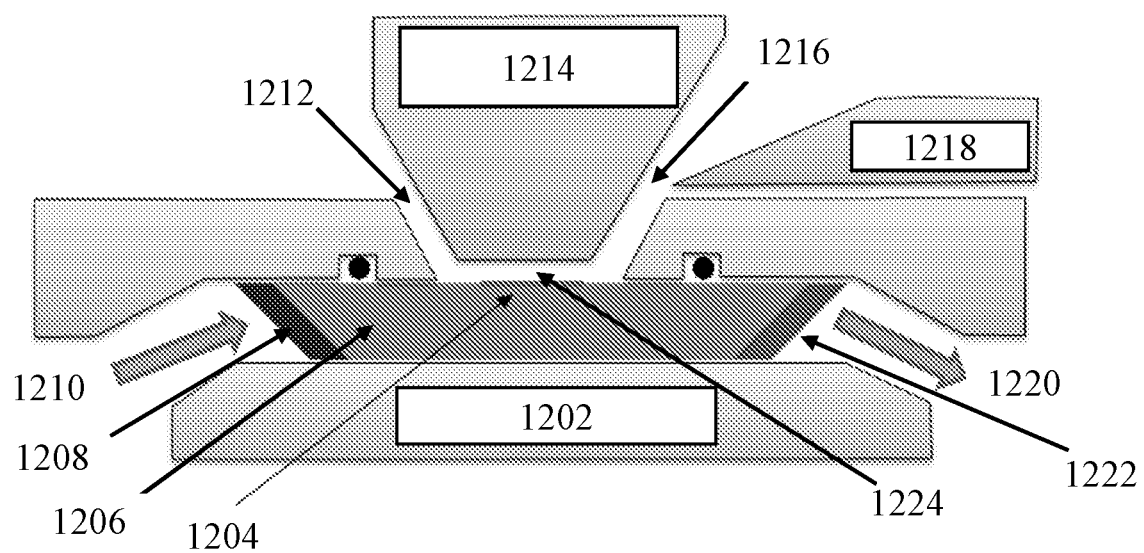
FIG. 12 is a schematic showing the structure of an ATR device in accordance with embodiments of the present disclosure.

With respect to FIG. 12, an ATR spectrometer built around the multi-faceted prism of FIGS. 11.1 and 11.2 is shown. The multi-faceted prism described in FIGS. 11.1 and 11.2 is shown installed at 1206 on a metallic pressure packing plate 1202 for mechanical support to achieve a suitable pressure rating. The guidance enhancement layer 1110 is located in the interface between the prism 1206 and the supporting plate 1202, wherein the guidance enhancement layer isolates the structure from the beam path and minimizes stresses against the body of prism 1206.

During measurement, incident light beam 1210 passes through the filter 1208, enters prism 1206, and exits as beam 1220. Upper metallic plate 1214 is positioned above prism 1206 and pressure sealed in place. The upper metallic plate 1214 has a small recess creating sample cell 1224 with the face of prism 1206. Two holes 1212 and 1216 present in the upper metallic plate 1214 permit flow of a sampled flow in and out of the structure. The area of sample cell 1224 is where the sample pressure is applied to prism, and is a small fraction of the area of prism 1206. This, in conjunction with the bottom face of prism 1206 being supported by pressure backing plate 1202, ensure the spectrometer can operate at high pressures without any mechanical damage to the prism or fluid entering the tool interior.

Fluid is directed onto the surface of the measurement structure through port 1216, and is guided by flow director 1218, which can be swapped out to match the measurement objectives to the characteristics of the oil and intended logging speed. For example, where measurements will be performed on stationary fluids, flow director 1218 design would limit circulation of the fluid to ensure a static and stable sample exists within the measurement period. For measurements on dynamic fluid samples, ports 1216 and 1212 and flow director 1218 may be designed to provide for turbulent fluid flow (flow having a relatively high Reynolds number) within the cell to ensure the sample volume is evacuated to ensure that subsequent measurements are performed on a new fluid sample.

In one or more embodiments, a spectrometer may utilize a dual measurement cell configuration, such as that described with respect to FIG. 13. For example, by modifying prism 1206 of FIG. 12 to the dual measurement cell multi-faceted prism 1300 shown in FIGS. 13.1 and 13.2. Dual measurement cell configurations may utilize single wavelength balanced detection on two detectors to reject common mode interferences.

The dual measurement cell prism of FIGS. 13.1 and 13.2, aside from the optical configuration, may have many of the same features as described with respect to FIGS. 11.1 and 11.2, such as different thin-film filters and anti-reflective coatings 1310. With respect to 13.1, the light input faces 1306 and 1308 are angled such that the two separate, non-intersecting, beampaths are generated and contact their respective sample windows 1302 and 1304. The two sample windows 1306 and 1308 may have different lengths, widths, and may probe differing fluid samples. Likewise, the filters on the faces 1306 and 1308 may be tailored to pass lights of the same or different frequencies. Operationally, a dual measurement cell prism 1300 may be installed into an ATR spectrometer, such as that described with respect to FIG. 12.

In one or more embodiments, a formation fluid may be separated into two phases (oil and water, for example) and both measured simultaneously using an ATR spectrometer equipped with a dual measurement cell prism 1300. In some embodiments, depending on the expected concentration of surface active species in each phase, the length and width of the windows 1302 and 1304 can be adjusted to provide desired signal level for each phase.

In one or more embodiments, an ATR spectrometer, such as that described in FIG. 12, may be equipped with a prism such as that described in FIG. 13 that generates beampaths having different operational wavelengths. For example, a first beam may be configured to analyze the carbonyl stretch peak at 1718 $cm^{-1}$ and measure the surface-active species, while a second beam may be centered in the range 1800-2200 $cm^{-1}$ and used for background measurement, as described above. In some embodiments, ATR spectrometers equipped with dual measurement cells may use a single detector to measure light reflected from each measurement cell, where the spectrometer uses a beam-selection mechanism to separately sample each beam.

The angle of the facets 1306 and 1308 are designed according to Snell's law to split an incoming collimated beam into two ATR paths within the same prism, propagating across the measurement window in two different directions. These two beams reach the back facets 1314 and 1312 respectively, and are then directed to two separate detectors (not shown). Filters are shown on both the entrance and exit faces of the structure, which may be thin-film filters or dichroics designed to select the measurement and reference frequency ranges. In some embodiments, filters may be present on both the entrance and exit faces. In some embodiments, a first facet may include a single filter or dichroic, while the exit facet employs an anti-reflection coating instead.

The prism may employ an optical guidance enhancement layer 1316 which has a lower refractive index in the spectral region of interest than the base optical prism material. For example, in the case of a germanium prism, the enhancement layer 1316 could be a layer of GeO2. As a result, the oxide layer may act as a guide and serves to limit access of the evanescent wave to the sample chamber. In one or more embodiments, a sensing window may be etched into the enhancement layer 1316 that is defined and matched to the system performance requirements, while the physical structure of the prism can be optimized for the mechanical arrangement, such as detector separation and mechanical resistance to pressure. The enhancement layer 1316 may allow seals to be placed on the front face of the structure, preventing access of fluids to the interior of the tool and preventing adhesives and sealing components from interfering with the optical measurements.

Devices incorporating ATR measurement techniques in accordance with the present disclosure may have advantages over direct transmission measurements in that only the surface of the prism forming the measurement cell is exposed to the sample, enabling a wider range of materials to be used in the construction of band-pass and anti-reflection thin-film interference filters, as these will not be exposed to a potentially corrosive fluid.

Methods in accordance with the disclosure may calibrate cell designs to determine the cell constants input to convert measured optical data to a concentration of surface active species present in the fluid in contact with the window. Calibration may also include characterization of beam-path degradation when used in field conditions, such as when studying a fluid downhole, and the establishment of degradation limits to provide user guidelines of when an optical cell is performing outside of specification and requires cleaning or replacement.

In one or more embodiments, direct measurement of acid species in samples may also include colorimetric measurements of carboxylic acid content of crude oils using any of the above described optical configurations. Colorimetric measurements operate using similar methods as described above with respect to IR-based techniques, with the modification that the optical system is tuned to detect the presence of chemical indicator produced by the reaction of a colorimetric dye with analytes in a sample fluid. For example, a colorimetric approach may measure the concentration of a colorimetric dye that has reacted with an organic acid or other surface-active species, as opposed to measuring the carbonyl stretching of an organic acid.

In some embodiments, colorimetric determination of acid concentration involves the added steps of: injecting analyte-specific dye components into a sample extracted from a hydrocarbon stream; mixing the dye components into the sample; and optimizing the optical system to detect the characteristic change in the dye spectrum, such as by adjusting the operating wavelength.

In one or more embodiments, direct measurement of acid species in samples may include detection of organic acid concentration using electrochemical methods in which a change in potential resulting from a reaction of an analyte-specific reagent with a surface-active species is used as a chemical indicator that is proportional to the surface-active species concentration in the sample. In some embodiments, analyte-specific reagents for electrochemical methods include quinone species and derivatives thereof such as benzoquinone.

Details regarding the measurement of organic acid concentration by electrochemical methods may be found, for example, in Liu et al., "A Method for the Determination of Weak Acid Concentration Based on Electrochemical Reduction of Benzoquinone, J. Electrochem. Soc., 2016, volume 163, issue 5, H373-H376.

In one or more embodiments, an electronically controlled element, such as a piezo-electric piston, or chamber expansion system, is employed to displace a volume of the analyte-specific reagent solution from an external reservoir into an injection chamber. In some embodiments, the electrically controlled element may operate with a system of two or more non-return valves to ensure that the analyte-specific reagent solution, rather than the sample fluid is displaced into the chamber. Analyte-specific reagents may be dispensed from a reservoir having a substantial capacity to administer tests and repeat testing. Reservoirs may be pressure balanced in some embodiments, such as through the use of a floating piston arrangement within the reservoir to maintain the sample cell at reservoir pressure, and minimize stress (mechanical, or thermal) on the injection components.

In one or more embodiments, systems incorporating analyte-specific reagent detection techniques may utilize thermal over-pressure methods to inject analyte-specific reagent at low temperatures and low pressures. Over-pressure methods may include heating a specific volume of dye solution above ambient temperatures to create sufficient pressure by constrained thermal expansion to inject a metered volume of the dye solution through a non-return valve system into the hydrocarbon sample chamber for subsequent optical, or electrochemical, detection.

In one or more embodiments, systems utilizing colorimetric techniques may inject analyte-specific reagents using medium to high pressure methods. In some embodiments, analyte-specific reagents may be injected using a piezoelectric "injection element" (or other electrically activated delivery mechanism) to create sufficient overpressure within the injection chamber to dispense a dose of analyte-specific reagent solution into the measurement cell and/or mixing chamber.

The injection element may be installed within a pressure balanced chamber, with electrical feedthroughs to allow drive, to ensure the element does not work against the wellbore hydrostatic pressure and minimize the size, complexity, reliability and electrical loading of the injection element and drive systems. This mechanism of injection has the advantage over the thermal injection mode that the solution is retained at ambient wellbore temperature, minimizing any potential degradation of the analyte-specific reagent that may occur by elevating its temperature.

In one or more embodiments, systems utilizing analyte-specific reagent techniques may incorporate features that aid mixing between a fluid sample and an injected analyte-specific reagent. In some embodiments, mixing may be accomplished by injecting a combined analyte-specific reagent/hydrocarbon solution through an orifice. For example, an orifice may form a connection to a secondary chamber through which the mixture is passed, at least once, before being transferred to a sample chamber for measurement.

In one or more embodiments, mixing may involve mechanical mixing of a sample fluid and an analyte-specific reagent by methods that include a blade or rotor-stator mixing scheme. In some embodiments, mechanical mixing may be performed by a magnetically coupled stirring system that drives to the stirring tool inside a sample chamber and maintains the stirring tool in the chamber in the event of mechanical shock or vibration.

In one or more embodiments, colorimetric dyes may be selected from commercially available chemicals and selected with regards to maximizing the optical signal (dependent on optical system design), maximizing the selectivity of the measurement, the volume to be stored, the degradation of the dye with temperature/pressure and/or time, and the toxicity thresholds for a given application.

Figure 14:
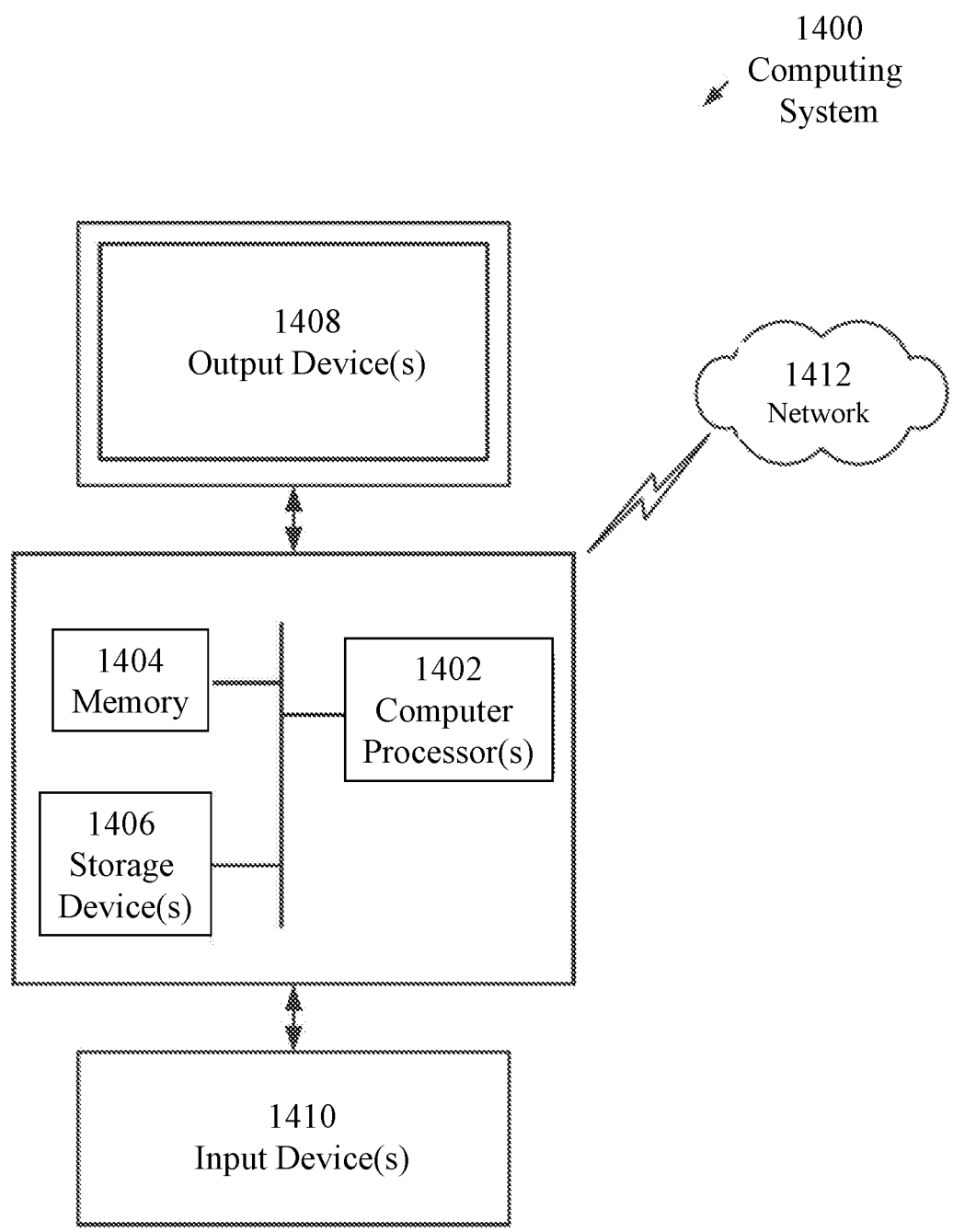
FIG. 14 is a schematic showing an example of a computer system for executing methods in accordance with the present disclosure.

Embodiments of the present disclosure may be implemented on a computing system. Any combination of mobile, desktop, server, embedded, or other types of hardware may be used. For example, as shown in FIG. 14, the computing system (1400) may include one or more computer processor(s) (1402), associated memory (1404) (e.g., random access memory (RAM), cache memory, flash memory, etc.), one or more storage device(s) (1406) (e.g., a hard disk, an optical drive such as a compact disk (CD) drive or digital versatile disk (DVD) drive, a flash memory stick, etc.) and numerous other elements and functionalities. The computer processor(s) (1402) may be an integrated circuit for processing instructions. For example, the computer processor(s) may be one or more cores, or micro-cores of a processor. The computing system (1400) may also include one or more input device(s) (1410), such as a touchscreen, keyboard, mouse, microphone, touchpad, electronic pen, or any other type of input device. Further, the computing system (1400) may include one or more output device(s) (1408), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (1400) may be connected to a network (1412) (e.g., a local area network (LAN), a wide area network (WAN) such as the Internet, mobile network, or any other type of network) via a network interface connection (not shown). The input and output device(s) may be locally or remotely (e.g., via the network (1412)) connected to the computer processor(s) (1402), memory (1404), and storage device(s) (1406). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the disclosure. Further, one or more elements of the aforementioned computing system may be located at a remote location and connected to the other elements over a network.

Further, embodiments of the disclosure may be implemented on a distributed system having a plurality of nodes, where each portion of the disclosure may be located on a different node within the distributed system. In one embodiment of the disclosure, the node corresponds to a distinct computing device. Alternatively, the node may correspond to a computer processor with associated physical memory. The node may alternatively correspond to a computer processor or micro-core of a computer processor with shared memory and/or resources.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112 (f) for any limitations of any of the claims herein, except for those in which the claim expressly uses the words 'means for' together with an associated function.

What is claimed:

1. A method, comprising:
   emplacing a downhole tool within a wellbore, wherein the downhole tool comprises a spectrometer having a dual measurement cell prism comprising first and second measurement cells having different cell lengths from each other, wherein the dual measurement cell prism comprises first and second sample windows having different lengths and widths from each other for sampling different fluid samples, and wherein the dual measurement cell prism comprises an optical guidance enhancement layer having a lower refractive index in a spectral region of interest than a base optical prism material of the dual measurement cell prism;

sampling a fluid at a downhole location within the wellbore with the downhole tool;
analyzing the fluid using the spectrometer; and
calculating an interfacial tension (IFT) for the fluid according to the formula:

$$\gamma = \gamma_{HC} + \gamma_{AB}$$

wherein $\gamma_{AB}$ is an acid-base IFT contribution and is equal to $$\gamma_{AB} = -RT\Gamma_m \ln(1 + K_L C)$$

wherein R is the gas constant, T is the temperature of a sample, $\Gamma_m$ is the maximum adsorption at equilibrium, $K_L$ is the Langmuir adsorption equilibrium constant, and C is the bulk volume concentration of surface active species in the fluid, and $\gamma_{HC}$ is a hydrocarbon fluid IFT contribution and is equal to $$\left( \frac{1.58(\rho_w - \rho_h) + 1.76}{T_r^{0.3125}} \right)^4$$

wherein $\rho_w$ and $\rho_h$ are the densities of water and hydrocarbon respectively, and $T_r$ is the reduced temperature, wherein the reduced temperature $T_r$ is a ratio of operating temperature to a pseudo-critical temperature of the water and hydrocarbon, and wherein calculating the acid-base IFT contribution comprises measuring the bulk volume concentration of the surface active species directly.

2. The method of claim 1, wherein the concentration of the surface active species is determined at the downhole location within the wellbore.

3. The method of claim 1, wherein the spectrometer is selected from a group consisting of: an infrared spectrometer, a visible spectrometer, an ultraviolet spectrometer, and a fluorescence spectrometer.

4. The method of claim 3, wherein the spectrometer is an infrared spectrometer configured to measure in the 1750-1700 cm$^{-1}$ range.

5. The method of claim 3, wherein the spectrometer is a transmission spectrometer or an attenuated total reflectance spectrometer.

6. The method of claim 3, wherein the spectrometer is configured to use alternating filters.

7. The method of claim 1, wherein analyzing the fluid comprises:
mixing an analyte-specific reagent with the fluid; and
measuring the concentration of a chemical indicator in the fluid, wherein the chemical indicator is produced by a reaction of the analyte-specific reagent and the surface active species in the fluid.

8. The method of claim 1, wherein the fluid comprises two or more selected from a group consisting of water, oil, and gas.

9. The method of claim 1, wherein the spectrometer is an attenuated total reflectance spectrometer configured to use a single detector to measure light reflected from each of the first and second measurement cells.

10. The method of claim 1, further comprising directing light to travel through each measurement cell from a respective angled light entrance facet to a respective angled light exit facet.

11. The method of claim 10, wherein the angled light entrance facet of each of the first and second measurement cells comprises a single filter or dichroic, and the angled light exit facet of each of the first and second measurement cells comprises an anti-reflection coating.

12. The method of claim 1, further comprising adjusting first and second flows of the fluid across the first and second sample windows using first and second adjustable inlet flow paths.

13. An apparatus for measuring an interfacial tension (IFT) in a fluid at a downhole location in a wellbore, the apparatus comprising a downhole tool, wherein the downhole tool comprises:
a sampling module to sample the fluid; and
a downhole fluid analysis module comprising a spectrometer configured to measure a concentration of a surface active species in the fluid, and a processor configured to control the operation of the spectrometer and to determine the IFT of the fluid at the downhole location within the wellbore based on the measured concentration of the surface active species, wherein the spectrometer comprises a dual measurement cell prism comprising first and second measurement cells having different cell lengths from each other, wherein the dual measurement cell prism comprises first and second sample windows having different lengths and widths from each other for sampling different fluid samples, and wherein the dual measurement cell prism comprises an optical guidance enhancement layer having a lower refractive index in a spectral region of interest than a base optical prism material of the dual measurement cell prism.

14. The apparatus of claim 13, wherein the downhole fluid analysis module comprises a transmission spectrometer or an attenuated total reflectance spectrometer.

15. The apparatus of claim 13, wherein the spectrometer is an attenuated total reflectance spectrometer configured to use a single detector to measure light reflected from each of the first and second measurement cells.

16. The apparatus of claim 13, wherein each of the first and second measurement cells comprises an angled light entrance facet and an angled light exit facet, wherein light travels through each measurement cell from a respective angled light entrance facet to a respective angled light exit facet.

17. The apparatus of claim 16, wherein the angled light entrance facet of each of the first and second measurement cells comprises a single filter or dichroic, and the angled light exit facet of each of the first and second measurement cells comprises an anti-reflection coating.

18. The apparatus of claim 13, wherein the dual measurement cell prism comprises first and second adjustable inlet flow paths configured to control first and second flows of the fluid across the first and second sample windows.

* * * * *